United States Patent [19]
Baum et al.

[11] Patent Number: 5,859,274
[45] Date of Patent: Jan. 12, 1999

[54] ANHYDROUS MONONUCLEAR TRIS(β-DIKETONATE) BISMUTH COMPOSITIONS FOR DEPOSITION OF BISMUTH-CONTAINING FILMS, AND METHOD OF MAKING THE SAME

[75] Inventors: Thomas H. Baum, New Fairfield; Gautam Bhandari, Danbury; Margaret Chappuis, New Milford, all of Conn.

[73] Assignee: Advanced Technology Materials, Inc., Danbury, Conn.

[21] Appl. No.: 960,915

[22] Filed: Oct. 30, 1997

[51] Int. Cl.[6] .................................................. C07F 9/94

[52] U.S. Cl. .............................................. 556/76; 556/64

[58] Field of Search ........................................ 556/64, 76

[56] References Cited

PUBLICATIONS

Fukin, et al. "Crystal and Molecular Structure of Bismuth Dipivaloylmethanate," Russian Journal of Inorganic Chemistry, vol. 38, No. 7 (1993), pp. 1119–1123.
CA:120:42314 abs of Zh Neorg Khim by Fukin, 38(7), pp.1205–1211, 1993.
CA:121:147729 abs of Koord Khim. by Zaharkova, 20(2) pp. 101–105, 1994.

Primary Examiner—Gary Geist
Assistant Examiner—Jean F. Vollano
Attorney, Agent, or Firm—Steven J. Hultquist; Oliver A. M. Zitzmann

[57] ABSTRACT

Anhydrous mononuclear tris(β-diketonato)bismuth complexes, useful as precursors for chemical vapor deposition of bismuth, for producing Bi-containing films of significantly improved stoichiometry, morphology and functional character, as compared to films obtained from dinuclear tris(β-diketonato)bismuth complexes of the prior art.

13 Claims, 6 Drawing Sheets

ANHYDROUS MONONUCLEAR TRIS(β-DIKETONATE) BISMUTH COMPOSITIONS FOR DEPOSITION OF BISMUTH-CONTAINING FILMS, AND METHOD OF MAKING THE SAME

BACKGROUND OF THE INVENTION

1. Field of the Invention

This invention relates to the synthesis and production of anhydrous mononuclear tris(β-diketonate) bismuth compositions, e.g., anhydrous mononuclear tris(2,2,6,6-tetramethyl-3,5-heptanedionato)bismuth. Such bismuth-containing compositions have utility as precursors for chemical vapor deposition of bismuth, bismuth oxide, bismuth-containing oxides and bismuth-containing chalcogonides.

2. Description of the Related Art

Ferroelectric random access memories (FRAMs) rely on high-integrity ferroelectric thin-films as critical components of memory cell architecture.

Electrical performance of ferroelectric oxides such as $SrBi_2Ta_2O_9$ (SBT) show a strong dependence on the identity of the precursor used in depositing the Bi component in the ferroelectric material. For example, the use of a Bi precursor such as triphenyl bismuth results in poor stoichiometric control, high substrate temperatures to decompose the precursor, strong surface dependence, and extreme dependence of the precursor incorporation efficiency on reactor pressure and partial pressure of oxygen during deposition.

To ameliorate the foregoing deficiencies, the art has continued to seek other bismuth precursors.

One such bismuth-containing precursor candidate is Bi tris(2,2,6,6-tetramethyl-3,5-heptanedionato). As used hereinafter, the ligand "2,2,6,6-tetramethyl-3,5-heptanedionato" is sometimes referred to by the designation "thd."

It is an object of the present invention to provide an improved class of bismuth precursors for deposition of Bi for applications such as ferroelectric thin films and devices.

Other objects and advantages of the present invention will be more fully apparent from the ensuing disclosure and appended claims.

SUMMARY OF THE INVENTION

The present invention relates to anhydrous mononuclear tris(β-diketonate)bismuth compositions, and to a method of synthesis thereof. Such anhydrous mononuclear bismuth precursors have been discovered as novel compositions having unexpectedly superior properties in relation to dinuclear (β-diketonate)bismuth compositions of the prior art, in respect of their volatilization and deposition characteristics which render the anhydrous mononuclear bismuth precursors of the present invention particularly suitable as CVD precursors. The anhydrous mononuclear bismuth compositions of the present invention therefore constitute a substantial advance in the art over the dinuclear tris(β-diketonate) bismuth precursors heretofore available.

The β-diketonato ligand of the anhydrous mononuclear tris(β-diketonate)bismuth compositions of the present invention may be any suitable type, including the illustrative β-diketonato ligand species set out in Table I below:

TABLE I

| β-diketonato ligand | Abbreviation |
| --- | --- |
| 2,2,6,6-tetramethyl-3,5-heptanedionato | thd |
| 1,1,1-trifluoro-2,4-pentanedionato | tfac |
| 1,1,1,5,5,5-hexafluoro-2,4-pentanedionato | hfac |
| 6,6,7,7,8,8,8-heptafluoro-2,2-dimethyl-3,5-octanedionato | fod |
| 2,2,7-trimethyl-3,5-octanedionato | tod |
| 1,1,1,5,5,6,6,7,7,7-decafluoro-2,4-heptanedionato | dfhd |
| 1,1,1-trifluoro-6-methyl-2,4-heptanedionato | tfmhd |

The anhydrous mononuclear tris(β-diketonato)bismuth compositions of the invention have utility as precursors for the vapor-phase deposition of bismuth, as for example in the formation of ferroelectric thin films of $SrBi_2Ta_2O_9$ (SBT), or in the formation of superconductor films containing Bi. In such applications, the use of the anhydrous mononuclear Bi source material provides for better thermal transport and flash vaporization leading to Bi-containing films of significantly improved stoichiometry, morphology and ferroelectric/superconducting character.

The synthesis of anhydrous mononuclear tris(β-diketonato)bismuth complexes of the present invention may be carried out in an aprotic solvent medium under anaerobic conditions, by reacting the corresponding Na(β-diketonato) compound with a Bi trihalide compound. Purification of the isolated reaction product bismuth complex, e.g., by recrystallization, should also be carried out in an aprotic medium under anaerobic conditions.

In a specific method aspect, the present invention relates to a method of synthesis of anhydrous mononuclear tris(2,2,6,6-tetramethyl-3,5-heptanedionato)bismuth, by reaction of Na(2,2,6,6-tetramethyl-3,5-heptanedionato) and $BiCl_3$ in an aprotic solvent under anaerobic conditions.

The anhydrous mononuclear tris(2,2,6,6-tetramethyl-3,5-heptanedionato)bismuth precursor of the invention may be usefully employed for depositing bismuth or a bismuth-containing film on a substrate, by vaporizing the anhydrous mononuclear tris(β-diketonato)bismuth to form a vaporized precursor, and contacting the vaporized precursor with the substrate to deposit bismuth or a bismuth-containing film thereon.

Such deposition may employ liquid delivery and flash vaporization of the anhydrous mononuclear tris(β-diketonato)bismuth precursor to form the precursor vapor, and the deposition may be effected by various techniques such as chemical vapor deposition (CVD), including any of various assisted (e.g., plasma-assisted, photoactivated, ion beam-assisted, etc.) CVD methods.

Other aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1:
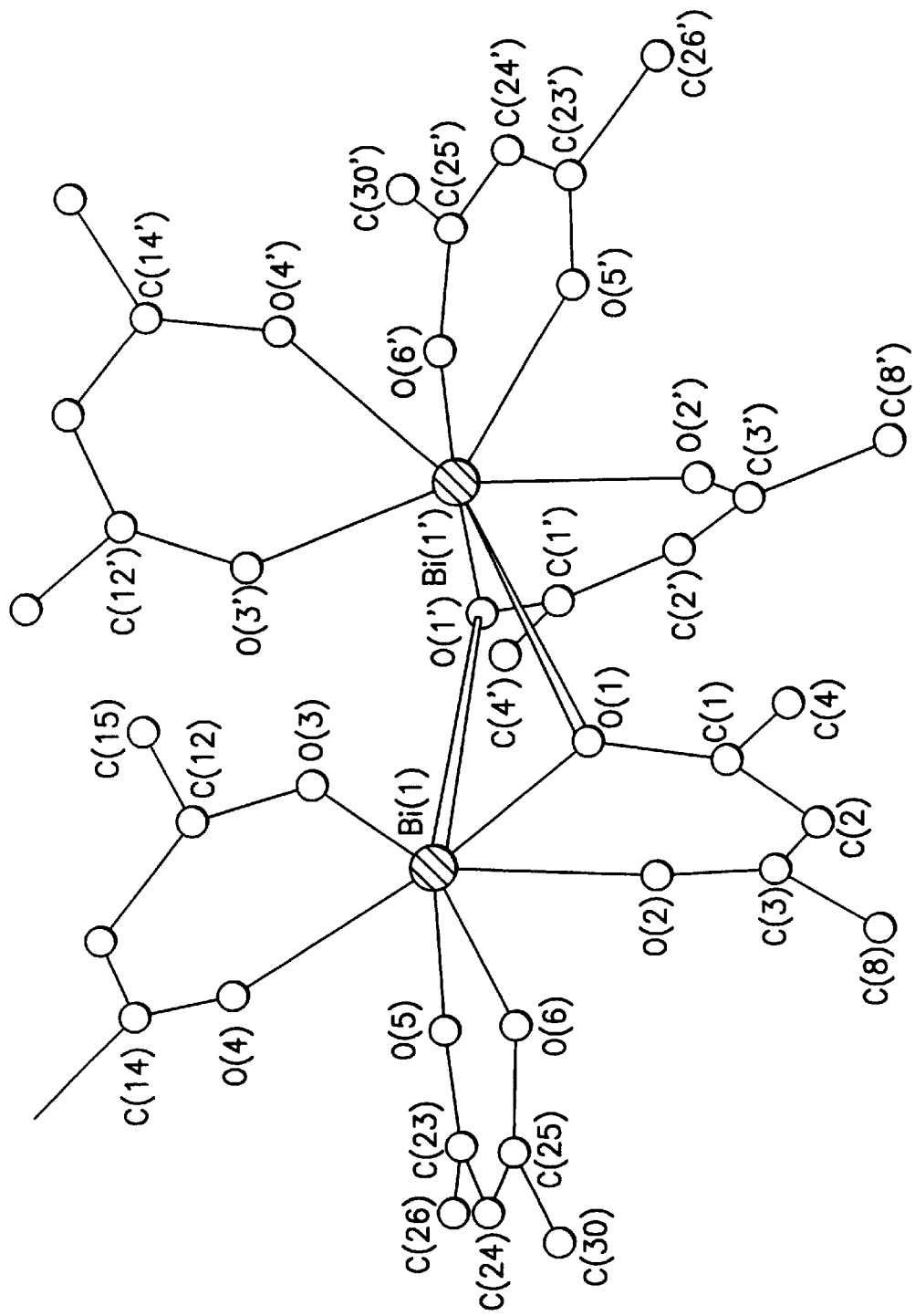
FIGS. 1 and 2 are x-ray crystallographic structural depictions reported in the literature (PRIOR ART) for the dinuclear bismuth complex $[Bi(thd)_3]_2$, which is a crystalline white solid with a melting point of 117° C.

The present invention relates to the discovery of anhydrous mononuclear forms of tris($\beta$-diketonato)bismuth compositions, e.g., tris(2,2,6,6-tetramethyl-3,5-heptanedionato)bismuth, which overcome deficiencies of the prior art dinuclear bismuth complex $[Bi(thd)_3]_2$.

As a result of its mononuclear form, the bismuth complex of the present invention provides improved thermal transport and more controlled and reproducible gas-phase concentrations than are possible with the prior art dinuclear complex. These characteristics provide the mononuclear bismuth complexes of the present invention with the ability to form Bi-containing films of superior stoichiometry, morphology and functional performance characteristics, in relation to the films of the prior art formed from the aforementioned dinuclear bismuth complex $[Bi(thd)_3]_2$.

As a precursor for the deposition of Bi or Bi-containing films, the previously commercially available dinuclear Bi-thd complex is markedly inferior in respect of its volatility, transport and vaporization properties, being less volatile and more easily decomposed during transport and flash vaporization than desired, and producing higher levels of residue in process equipment upstream of the deposition chamber. The ready susceptibility of the prior art dinuclear bismuth complex $[Bi(thd)_3]_2$ to decomposition of the precursor is severely detrimental in a liquid delivery flash vaporization process, where such decomposition leads to premature clogging of the vaporizer as well as undesirable changes in gas-phase concentrations during the deposition process. Such gas-phase concentration variations in turn yield undesirable gradients in deposited film thickness, and in film stoichiometry where the bismuth component is deposited in a multicomponent film.

Unexpectedly, the discovery of the mononuclear Bi($\beta$-diketonate)$_3$ complexes of the present invention has provided a solution to such deficiencies of the prior art Bi(thd)$_3$ precursor material. The mononuclear Bi($\beta$-diketonate)$_3$ complexes of the present invention are markedly superior to the corresponding dinuclear species, providing improved vaporizer performance, extended vaporizer lifetimes and better control of the Bi-containing film stoichiometry than $[Bi(thd)_3]_2$. As a result, the Bi($\beta$-diketonate)$_3$ mononuclear complexes of the present invention lead to a more highly reproducible CVD process and improved quality of the deposited film, based on film stoichiometry and uniformity.

While the anhydrous mononuclear tris($\beta$-diketonato) bismuth complexes of the present invention are usefully employed in a wide variety of chemical vapor deposition processes for the formation of bismuth-containing films, the complexes have particular utility as a precursor for the vapor-phase deposition of bismuth or bismuth oxide in the formation of ferroelectric thin films and Bi-based superconducting thin film materials. A most preferred use of such mononuclear tris($\beta$-diketonato)bismuth complexes is in the formation of ferroelectric Bi-containing thin films for the manufacture of devices such as ferroelectric random access memories. The same materials may be used to deposit bismuth-containing chalcogenides and skutteurdites.

The mononuclear tris($\beta$-diketonato)bismuth complexes of the invention may be. deposited in any suitable manner. For example, the bismuth deposition process may employ liquid delivery and flash vaporization of the anhydrous mononuclear tris($\beta$-diketonato)bismuth precursor to form the precursor vapor, and the deposition itself may be effected by chemical vapor deposition (CVD), including any of various assisted (e.g., plasma-assisted) CVD methods, or in any other suitable manner. For purposes of liquid delivery, the anhydrous mononuclear tris($\beta$-diketonato)bismuth may be dissolved in any suitable solvent medium, e.g., a single solvent or a multicomponent solvent mixture, compatible with such bismuth reagent.

A suitable multicomponent solvent mixture for such purpose is a solvent composition comprising solvent species A, B and C, wherein A is a $C_6$–$C_8$ alkane, B is a $C_8$–$C_{12}$ alkane, and C is a glyme-based solvent (glyme, diglyme, tetraglyme, etc.) or a polyamine, in the proportion A:B:C wherein A is from about 3 to about 7 parts by volume, B is from about 2 to about 6 parts by volume, and C is from 0 to about 3 parts by volume.

A highly preferred solvent composition of such type comprises octane, decane and a polyamine in approximately 5:4:1 proportion by volume. Polyamine species potentially useful as component C in the above-described solvent composition include N,N,N',N'-tetramethylethylenediamine, N,N,N',N",N"-pentamethyldiethylenetriamine, N,N,N',N",N'",N'"-hexamethyltriethylenetetramine, or other suitable polyamine component.

The synthesis of anhydrous mononuclear tris ($\beta$-diketonato)bismuth complexes of the present invention may be readily carried out in an aprotic solvent medium under anaerobic conditions, and at room temperature and pressure, by reaction of the corresponding Na($\beta$-diketonato) compound with $BX_3$, wherein X is halo (bromo, chloro, iodo, or fluoro), and most preferably chloro. Purification of the isolated reaction product bismuth complex, e.g., by recrystallization, is also advantageously performed in an aprotic medium under anaerobic conditions.

The aprotic solvent may suitably comprise one or more alkanes such as pentane, octane, or decane, aliphatic or cyclic ethers such as tetrahydrofuran, aryl solvent species such as benzene or toluene, and/or any other suitable aprotic solvent(s) for solution of the Na($\beta$-diketonato) and $BiX_3$ starting materials, wherein such solvents do not preclude the reaction of such Na($\beta$-diketonato) and $BiX_3$ starting materials to form the mononuclear ($\beta$-diketonato)bismuth product.

The foregoing synthesis reaction is carried out under anaerobic conditions, i.e., in the substantial absence, and preferably substantially complete absence, of oxygen. Such anaerobic conditions may for example comprise carrying out the reaction under inert or oxygen-free atmosphere, such as under a nitrogen or argon blanket over the reaction vessel containing the reactants and the aprotic solvent medium.

Similarly, the solvents and reactants should be dry and free from water and other protic source constituents.

As an illustrative example of the foregoing synthesis, anhydrous mononuclear tris(2,2,6,6-tetramethyl-3,5-heptanedionato)bismuth may be synthesized in accordance with the present invention by reaction of Na(2,2,6,6-tetramethyl-3,5-heptanedionato) with $BiCl_3$ in octane, and under a nitrogen gas environment.

Subsequent to its synthesis, the anhydrous mononuclear tris (β-diketonato)bismuth complexes of the invention may be converted to the corresponding dinuclear species, if desired, by exposure of the mononuclear tris (β-diketonato) bismuth complex to air and/or protic media such as water, isopropanol, etc.

Figure 2:
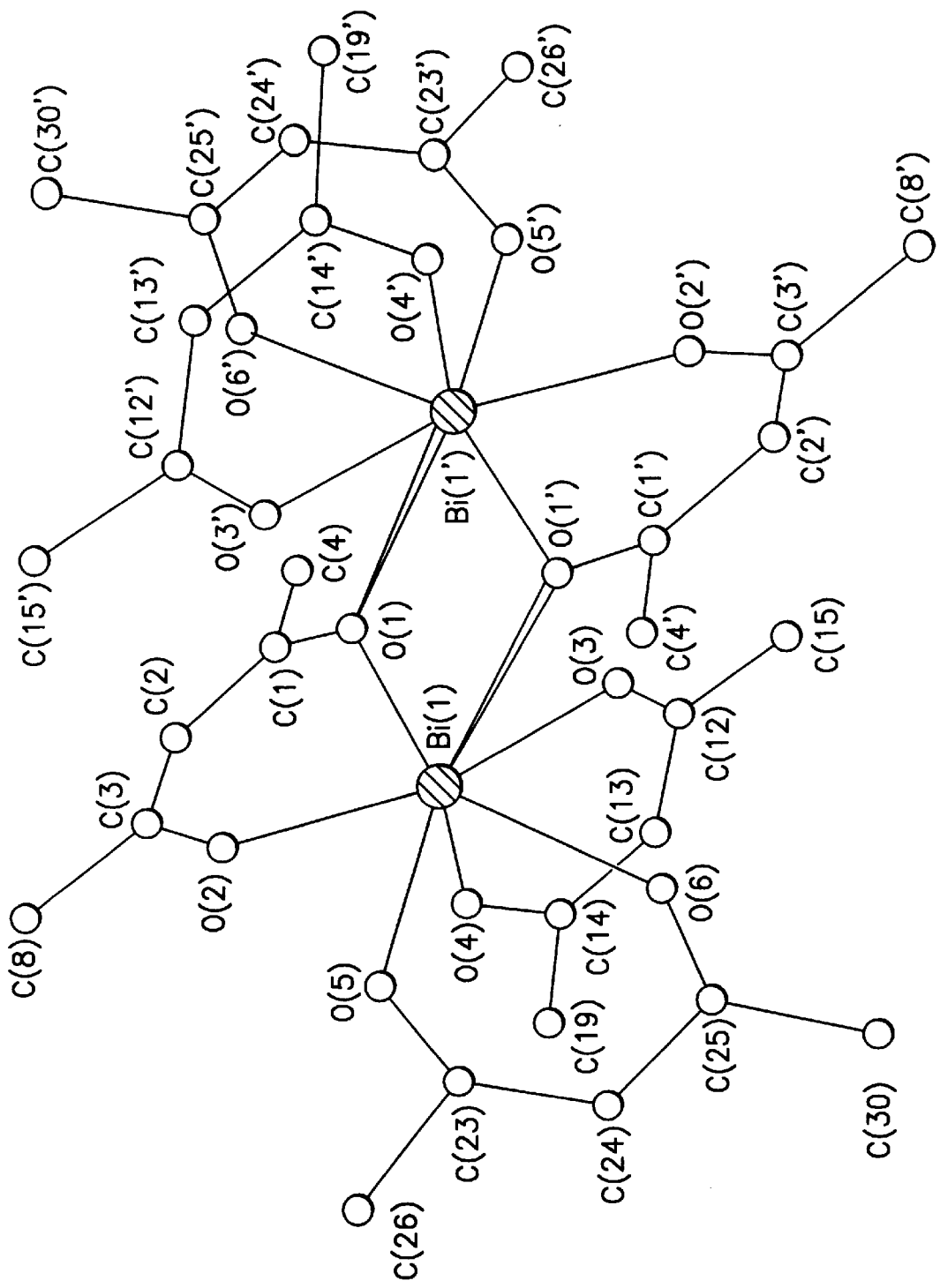

Referring now to the drawings, FIGS. 1 and 2 are x-ray crystallographic structural depictions reported in the literature (PRIOR ART) for the dinuclear bismuth complex $[Bi(thd)_3]_2$, which is a crystalline white solid with a melting point of 117° C.

Figure 3:
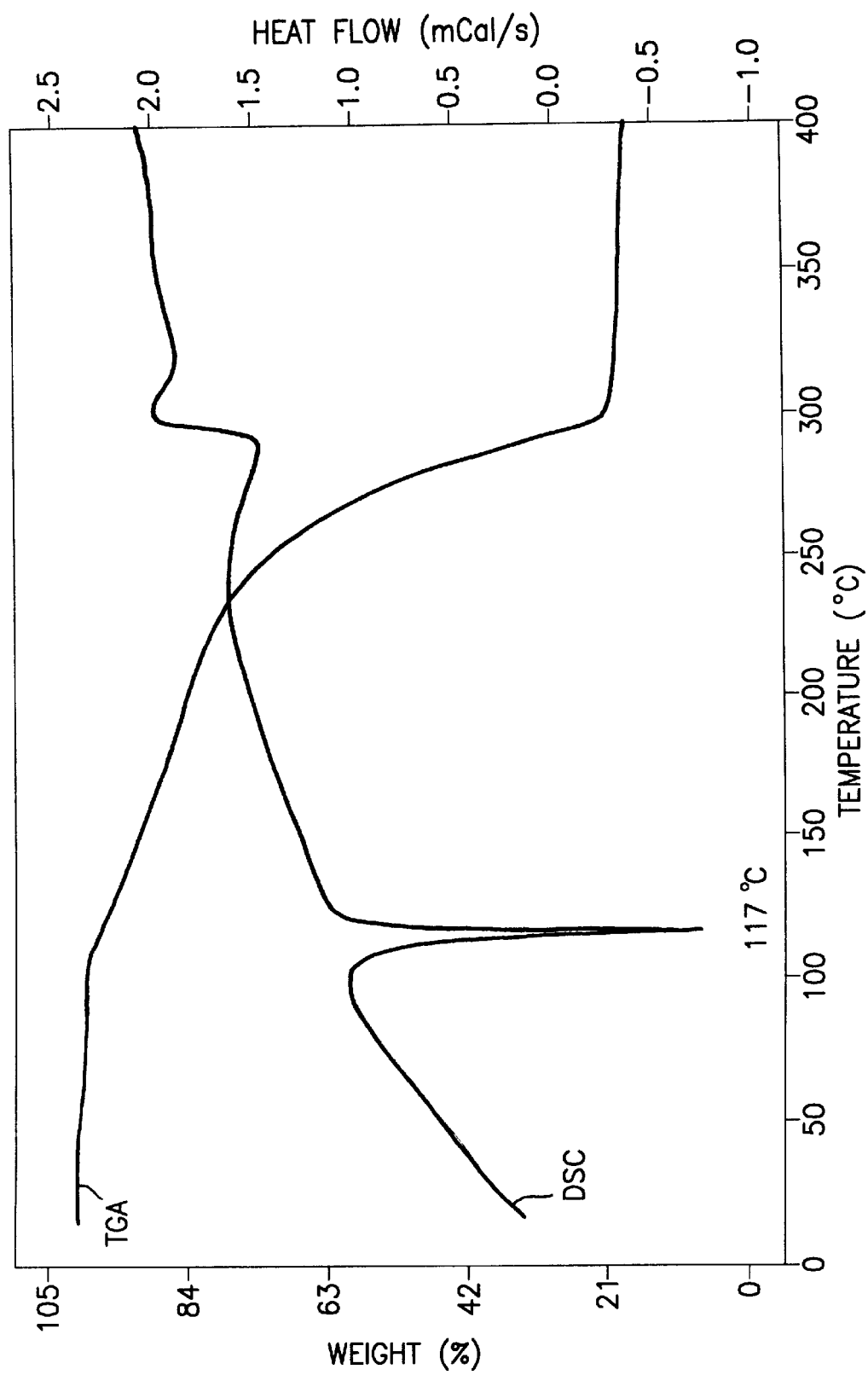
FIG. 3 is a plot of precursor transport (TGA) and melting point (DSC) curves for a representative dinuclear bismuth complex $[Bi(thd)_3]_2$ of the prior art.

FIG. 3 is a plot of precursor transport (TGA) and melting point (DSC) curves for a representative dinuclear bismuth complex $[Bi(thd)_3]_2$ of the prior art, having a melting point of 117° C. The literature has variously reported the melting point of such material as being in the range of 112°–115° C. This material is inferior in precursor transport properties, as reflected by the TGA plot, showing a gradual weight loss over a wide temperature range during the STA examination.

Figure 4:
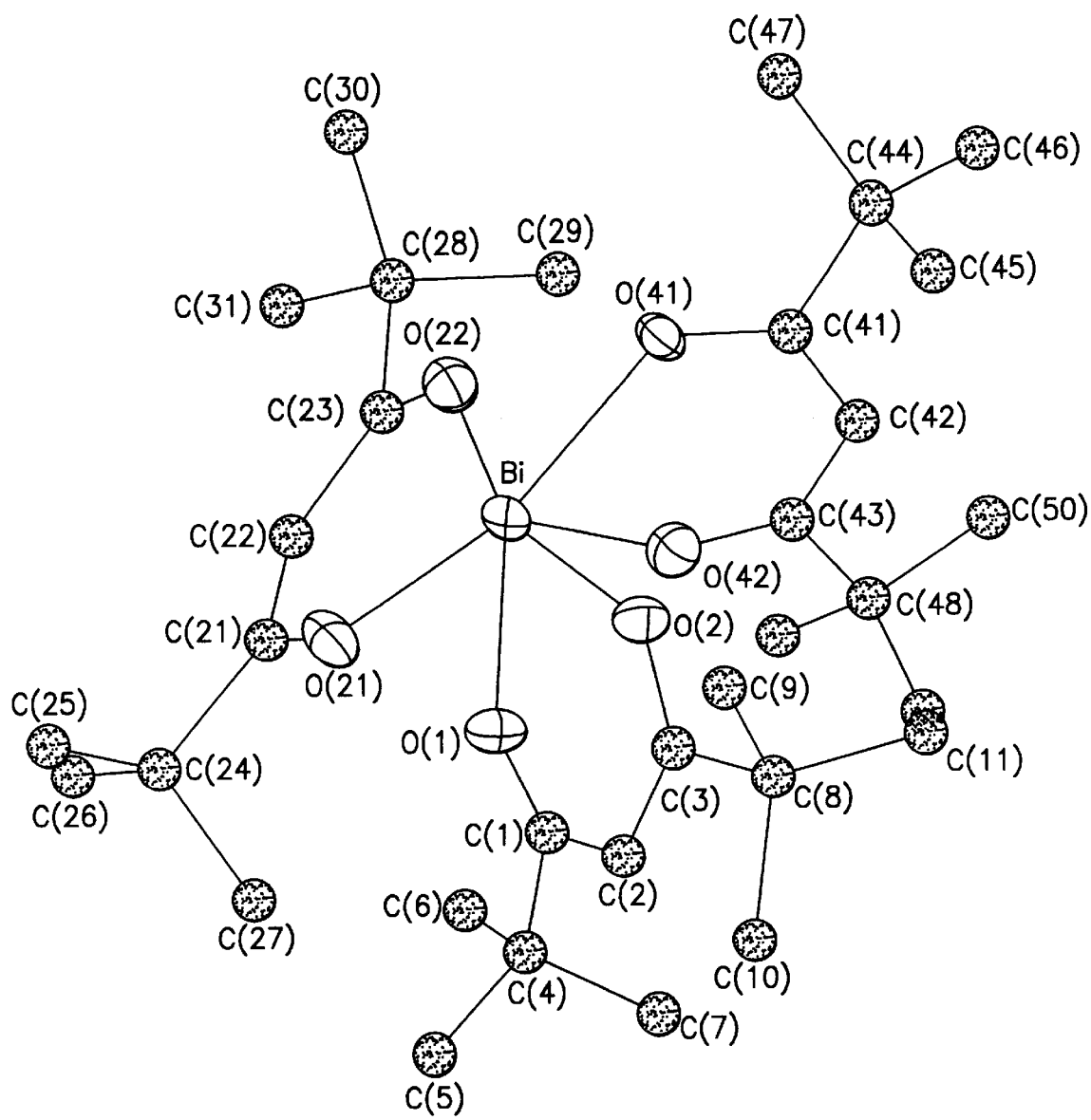
FIG. 4 is an x-ray crystallographic structural depiction for the anhydrous mononuclear tris(2,2,6,6-tetramethyl-3,5-heptanedionato)bismuth complex of the present invention. This material represents a new form of $Bi(thd)_3$.

FIG. 4 is an x-ray crystallographic structural depiction for the anhydrous mononuclear tris(2,2,6,6-tetramethyl-3,5-heptanedionato)bismuth complex of the present invention. This material represents a new form of $Bi(thd)_3$.

Figure 5:
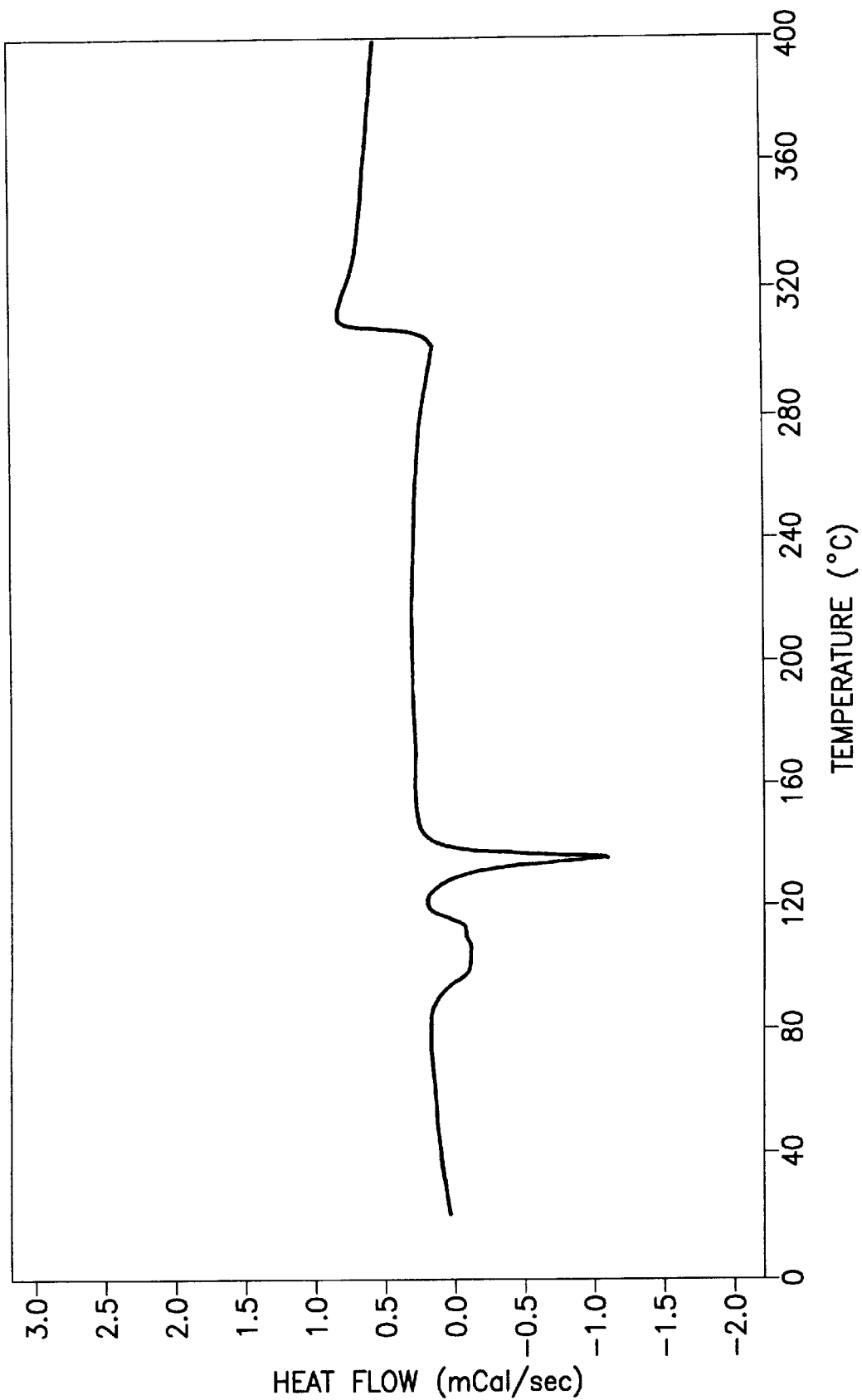
FIG. 5 is a plot of a melting point (DSC) curve for anhydrous mononuclear tris(2,2,6,6-tetramethyl-3,5-heptanedionato)bismuth complex of the present invention, exhibiting a melting point of about 139° C.

FIG. 5 is a plot of a melting point (DSC) curve for anhydrous mononuclear tris(2,2,6,6-tetramethyl-3,5-heptanedionato)bismuth complex of the present invention, exhibiting a melting point of about 139° C. The IR and NMR characteristics of this material are consistent with the mononuclear character of $Bi(thd)_3$.

Figure 6:
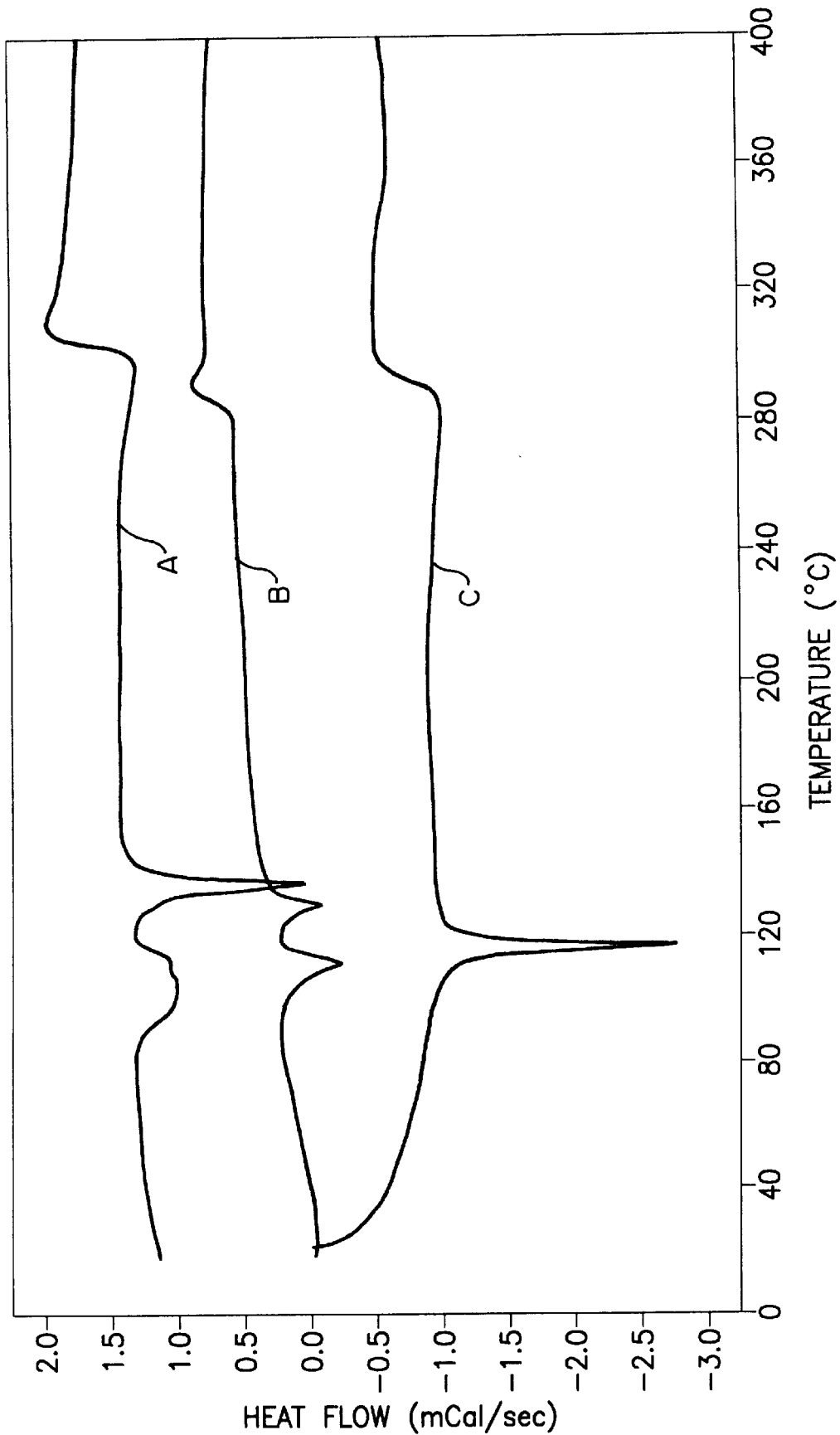
FIG. 6 is a plot of melting point (DSC) curves for the anhydrous mononuclear tris(2,2,6,6-tetramethyl-3,5-heptanedionato)bismuth complex of the present invention in "fresh" synthesized condition (curve A), after exposure to air/moisture for 48 hours (curve B) and after exposure to air/moisture for 96 hours (curve C), showing the complete conversion of the anhydrous mononuclear tris(2,2,6,6-tetramethyl-3,5-heptanedionato)bismuth complex after 96 hours of air/moisture exposure into the lower melting point dinuclear tris(2,2,6,6-tetramethyl-3,5-heptanedionato) bismuth complex, $[Bi(thd)_3]_2$.

FIG. 6 is a plot of melting point (DSC) curves for the anhydrous mononuclear tris(2,2,6,6-tetramethyl-3,5-heptanedionato)bismuth complex of the present invention in "fresh" synthesized condition (curve A), after exposure to air/moisture for 48 hours (curve B) and after exposure to air/moisture for 96 hours (curve C), showing the complete conversion of the anhydrous mononuclear tris(2,2,6,6-tetramethyl-3,5-heptanedionato)bismuth complex after 96 hours of air/moisture exposure into the lower melting point dinuclear tris(2,2,6,6-tetramethyl-3,5-heptanedionato) bismuth complex, $[Bi(thd)_3]_2$.

Thus, ambient air/moisture exposure gradually converts the mononuclear precursor to the lower melting dinuclear material having a melting point in the range of 117°–120° C. Prolonged direct air exposure over an extended period of time is also observed to result in the formation of a white, wet solid and eventually a clear liquid. The dissolution of solid mononuclear $Bi(thd)_3$ material in isopropanol or other protic solvent has also been found to effect a conversion of the mononuclear material to the dinuclear complex, $[Bi(thd)_3]_2$.

Single crystal x-ray diffraction structural determination conclusively show the $Bi(thd)_3$ material of the present invention to be of mononuclear form. Such material has a melting point which is more than 20° C. above that reported in the literature. The prior art literature reports an x-ray crystal structure which is a dinuclear complex, $[Bi(thd)_3]_2$, with excess Hthd ligand in the crystal lattice. The prior art literature reports the previously known Bi-thd complex as being air and moisture stable. This is untrue for the dinuclear complex, $[Bi(thd)_3]_2$, and is also untrue for the anhydrous mononuclear $Bi(thd)_3$ material of the present invention, as shown in the plot of FIG. 6. The mononuclear $Bi(thd)_3$ can be converted to the known dinuclear complex, $[Bi(thd)_3]_2$ by air exposure or exposure to protic media such as isopropanol.

The $Bi(thd)_3$ material of the present invention thus is a mononuclear complex heretofore unknown, and represents a significant advance in the art in the provision of a precursor material having highly attractive characteristics for vaporization, vapor-phase transport, and bismuth deposition, in a wide variety of applications in which bismuth or bismuth-containing films are employed in the fabrication of microelectronic, ferroelectric and superconducting devices or structures.

Although the invention has been variously disclosed herein with reference to illustrative embodiments and features, it will be appreciated that the embodiments and features described hereinabove are not intended to limit the invention, and that other variations, modifications and other embodiments will suggest themselves to those of ordinary skill in the art. The invention therefore is to be broadly construed, consistent with the claims hereafter set forth.

What is claimed is:

1. Anhydrous mononuclear tris(β-diketonato)bismuth.

2. An anhydrous mononuclear tris(β-diketonato)bismuth complex, wherein the β-diketonato ligand is selected from the group consisting of:

2,2,6,6-tetramethyl-3,5-heptanedionato;
   1,1,1-trifluoro-2,4-pentanedionato;
   1,1,1,5,5,5-hexafluoro-2,4-pentanedionato;
   6,6,7,7,8,8,8-heptafluoro-2,2-dimethyl-3,5-octanedionato;
   2,2,7-trimethyl-3,5-octanedionato;
   1,1,1,5,5,6,6,7,7,7-decafluoro-2,4-heptanedionato; and
   1,1,1-trifluoro-6-methyl-2,4-heptanedionato.

3. Anhydrous mononuclear tris(2,2,6,6-tetramethyl-3,5-heptanedionato)bismuth.

4. Tris(2,2,6,6-tetramethyl-3,5-heptanedionato)bismuth having a melting point of about 139° C.

5. Tris(2,2,6,6-tetramethyl-3,5-heptanedionato)bismuth having the x-ray crystallographic structure shown in FIG. 4.

6. A method of synthesis of an anhydrous mononuclear tris (β-diketonato)bismuth complex, comprising reacting a corresponding Na(β-diketonato) compound with a Bi trihalide compound in an aprotic solvent medium under anaerobic conditions for sufficient time and at sufficient temperature to yield said anhydrous mononuclear tris (β-diketonato) bismuth complex as a reaction product thereof.

7. A method according to claim 6, wherein the aprotic solvent medium comprises a solvent selected from the group consisting of alkanes, aliphatic ethers, cyclic ethers, and aryl compounds.

8. A method according to claim 6, wherein the aprotic solvent medium comprises a solvent selected from the group consisting of pentane, octane, decane, tetrahydrofuran, benzene and toluene.

9. A method according to claim 6, wherein the Na(β-diketonato) compound comprises a β-diketonato moiety selected from the group consisting of:

2,2,6,6-tetramethyl-3,5-heptanedionato;
   1,1,1-trifluoro-2,4-pentanedionato;
   1,1,1,5,5,5-hexafluoro-2,4-pentanedionato;
   6,6,7,7,8,8,8-heptafluoro-2,2-dimethyl-3,5-octanedionato;

2,2,7-trimethyl-3,5-octanedionato;

1,1,1,5,5,6,6,7,7,7-decafluoro-2,4-heptanedionato; and 1,1,1-trifluoro-6-methyl-2,4-heptanedionato.

10. A method according to claim 6, wherein the Bi trihalide compound is $BiCl_3$.

11. A method of synthesis of anhydrous mononuclear tris(2,2,6,6-tetramethyl-3,5-heptanedionato)bismuth, comprising reaction of Na(2,2,6,6-tetramethyl-3,5-heptanedionato) and $BiCl_3$ in an aprotic solvent medium under anaerobic conditions.

12. A method according to claim 11, wherein the aprotic solvent medium comprises a solvent selected from the group consisting of alkanes, aliphatic ethers, cyclic ethers, and aryl compounds.

13. A method according to claim 11, wherein the aprotic solvent medium comprises a solvent selected from the group consisting of pentane, octane, decane, tetrahydrofuran, benzene and toluene.

* * * * *

UNITED STATES PATENT AND TRADEMARK OFFICE
CERTIFICATE OF CORRECTION

PATENT NO : 5,859,274

DATED : January 12, 1999

INVENTOR(S) : Baum et al.

It is certified that error appears in the above-identified patent and that said Letters Patent is hereby corrected as shown below:

Column 4, Line 12, change "be." to -- be --

Signed and Sealed this

Thirty-first Day of August, 1999

*Attest:*

Q. TODD DICKINSON

*Attesting Officer*  Acting Commissioner of Patents and Trademarks